(12) United States Patent
Watanabe et al.

(10) Patent No.: US 6,659,943 B2
(45) Date of Patent: Dec. 9, 2003

(54) ENDOSCOPIC BATTERY-POWERED LIGHT SOURCE HAVING ROTATIONALLY-CHANGING RELATIVE POSITIONAL RELATIONSHIP WITH CONTROL SECTION OF ENDOSCOPE AND ENDOSCOPE APPARATUS COMPRISING THE ENDOSCOPIC BATTERY-POWERED LIGHT SOURCE

(75) Inventors: Katsushi Watanabe, Hachioji (JP); Itaru Osaki, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 10/098,938

(22) Filed: Mar. 15, 2002

(65) Prior Publication Data

US 2002/0137987 A1 Sep. 26, 2002

(30) Foreign Application Priority Data

Mar. 22, 2001 (JP) .......................... 2001-083001
Mar. 1, 2002 (JP) .......................... 2002-056297

(51) Int. Cl.[7] ................................................. A61B 1/06
(52) U.S. Cl. ....................................................... 600/178
(58) Field of Search ................................ 600/178, 179, 600/199, 200

(56) References Cited

U.S. PATENT DOCUMENTS 3,315,207 A * 4/1967 Speelman .................... 338/68
6,135,947 A   10/2000 Watanabe et al.

FOREIGN PATENT DOCUMENTS

JP          11-153759          6/1999

* cited by examiner

Primary Examiner—John Mulcahy
(74) Attorney, Agent, or Firm—Scully, Scott, Murphy & Presser

(57) ABSTRACT

A battery-powered light source in which the relative position to a control section of an endoscope is changed to switch an illumination lamp to an ON state or OFF state includes a light source main body containing a battery for supplying electric power for turning on the illumination lamp, a plurality of switch positions provided in a range in which the relative position between the light source main body and the control section of the endoscope is changed, and a click mechanical portion provided at at least one of the switch positions, for maintaining the relative position between the light source main body and the control section of the endoscope in a predetermined state and switching the illumination lamp to a predetermined state while maintaining the state of the relative position.

12 Claims, 14 Drawing Sheets

ENDOSCOPIC BATTERY-POWERED LIGHT SOURCE HAVING ROTATIONALLY-CHANGING RELATIVE POSITIONAL RELATIONSHIP WITH CONTROL SECTION OF ENDOSCOPE AND ENDOSCOPE APPARATUS COMPRISING THE ENDOSCOPIC BATTERY-POWERED LIGHT SOURCE

This application claims benefit of Japanese Applications No. 2001-083001 filed on Mar. 22, 2001, and No. 2002-056297 filed on Mar. 1, 2002, the contents of which are incorporated by this reference.

BACKGROUND OF THE INVENTION

1. Field of the Invention

The present invention relates to an endoscope apparatus comprising an endoscopic battery-powered light source detachably mounted on an endoscope.

2. Description of the Related Art

Endoscopes have been widely used in the medical field and the industrial field. Endoscopic diagnosis and examination require illumination means because an object to be examined is located in the interior of a living body, a plant, or the like. Therefore, an ordinary endoscope is provided with a light source device as an endoscopic external device.

The light source device contains a lamp, and the illumination light emitted from the lamp is guided to a light guide fiber or the like provided in the endoscope. The illumination light guided to the light guide fiber emerges from an illumination window provided at the distal end of an insertion portion to illuminate an examination site. In the light source device, light is emitted from the lamp by using power supplied from a commercial power supply.

On the other hand, Japanese Unexamined Patent Publication No. 11-153759 discloses an endoscope apparatus comprising a battery-powered light source which uses a dry battery as a power supply and which is detachably attached to a control section of the endoscope. The endoscope provided with the battery-powered light source can be easily carried and used in a place without a power supply, and thus the endoscope is suitable for use in an emergency.

The lamp provided in the battery-powered light source is turned on and off by changing the relative position between the battery-powered light source and the control section of the endoscope after the battery-powered light source is mounted on the control section of the endoscope. This makes it possible to determine from a glance at the appearance whether or not the lamp is turned on. Also, two switch positions are provided for ON and OFF states, and are respectively regulated by both ends of a rotating operation range in which the relative position is changed.

However, in the endoscope apparatus disclosed in Japanese Unexamined Patent Publication No. 11-153759, the switch positions are regulated only by a rotation operation. Therefore, the ON and OFF positions of the lamp are fixed. Therefore, in lighting of the lamp, the battery-powered light source possibly interferes with gripping or operation according to the user's way of gripping the control section of the endoscope.

In addition, when a switch position as a third switch besides the above ON and OFF states is provided in the rotating operation range according to a specified function such as the function to increase the duration time of the battery by decreasing the quantity of light to a level lower than that in the ON state, or the like in order to improve the function of the battery-powered light source, the operation of maintaining the specified function is very difficult. This is because there is no position fixing means for fixing the relative positional relationship between the battery-powered light source and the control section to another state in the rotating operation range. Therefore, even when the third switch is provided in the rotating operation range, the problem of improper moving of the switch position possibly occurs to deteriorate operability.

SUMMARY OF THE INVENTION

Accordingly, a first object of the present invention is to provide an endoscopic battery-powered light source permitting a change in the relative position between the battery-powered light source and a control section to obtain good operability.

A second object of the present invention is to provide an endoscopic battery-powered light source comprising another switch position provided in a rotation operation range in which the relative position between the battery-powered light source and a control section is changed, for switching the function to a predetermined state.

A third object of the present invention is to provide an endoscopic battery-powered light source with excellent operability, capable of stably maintaining the relative position between the battery-powered light source and a control section when being rotated to another switch position.

An endoscopic battery-powered light source of the present invention in which the relative position to a control section of an endoscope is changed to switch an illumination lamp to an ON state or OFF state comprises a light source main body containing a battery for supplying electric power for lighting the illumination lamp, a plurality of switch positions provided in a range in which the relative position between the light source main body and the control section of the endoscope is changed, a click mechanical portion provided at at least one of the switch positions, for maintaining the relative position between the light source main body and the control section of the endoscope in a predetermined state and switching the illumination lamp to a predetermined state while maintaining the state of the relative position. Therefore, by providing the click mechanical portion at a switch position within the range in which the relative position is changed, a switch position can be provided at a position besides the regulation positions in the range in which the relative position is changed. Also, a desired function can be given to each of the switch positions, and the functions can easily be switched.

The above and other objects, features and advantages of the invention will become more clearly understood from the following description referring to the accompanying drawings.

DETAILED DESCRIPTION OF THE PREFERRED EMBODIMENT

Embodiments of the present invention will be described below with reference to FIGS. 1 to 19.

Figure 1:
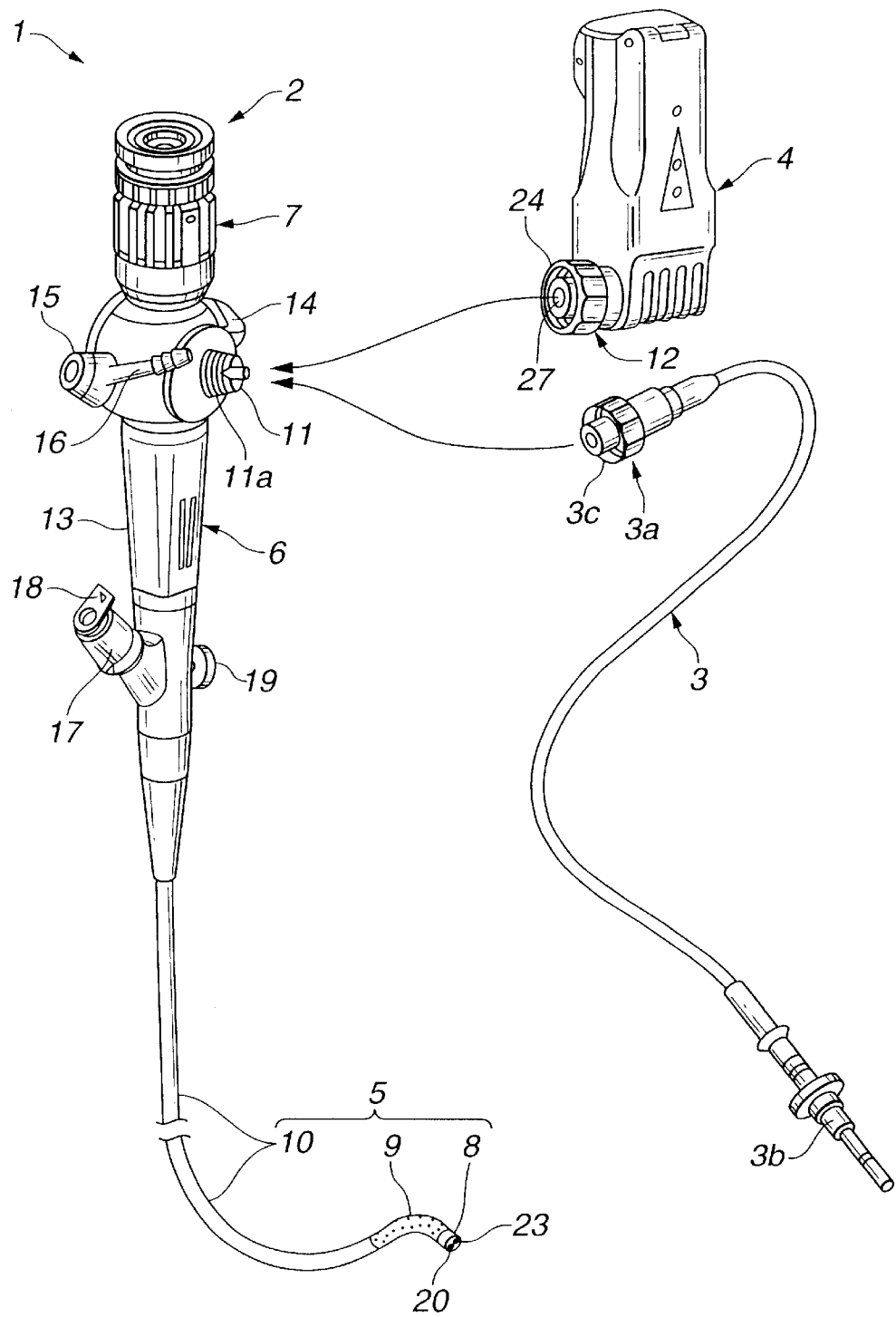
FIG. 1 is a drawing illustrating the configuration of an endoscope apparatus.

As shown in FIG. 1, an endoscope apparatus 1 comprises a water-tight endoscope 2, a light guide cable 3 detachably connected to the endoscope 2, a water-tight endoscopic battery-powered light source (referred to as a "battery-powered light source" hereinafter) 4.

The endoscope 2 comprises an elongated insertion portion 5, a control section 6 provided at the base end of the insertion portion 5, and an eyepiece portion 7 provided at the proximal end of the control section 6. The insertion portion 5 comprises-a hard tip 8, a bendable portion 9, and a flexible tube 10, which are sequentially provided.

A light guide connector 11 made of a member having high thermal conductivity is provided on the side of the control section 6 so as to laterally project. Furthermore, a connecting portion 3a of the light guide cable 3 or a connecting portion 12 of the battery-powered light source 4 is detachably connected to the light guide connector 11.

The control section 6 comprises a grip portion 13 to be gripped by an operator. The light guide connector 11, a bending operation lever 14 for bending the bendable portion 9, and a suction button 15 for performing a suction operation are provided on the proximal end of the grip portion 13. Furthermore, a suction connector 16 projects from the vicinity of the base end of the suction button 15 so as to communicate with a suction channel (not shown in the drawing) provided on the endoscope 2. The suction connector 16 is connected to a suction device (not shown in the drawing) through a tube not shown in the drawing. Therefore, when the suction button 15 is appropriately operated, body fluids in a body cavity can be discharged by suction through the suction channel and the suction connector 16.

Furthermore, a forceps insertion port 17 is provided to project from the front side of the grip portion 13. The forceps insertion port 17 is generally closed by a forceps valve 18. Also, for example, a ventilating connector 19 is provided on the opposite side of the forceps insertion port 17. A water leakage of the endoscope 2 can be checked by sending air into the endoscope 2 through the ventilating connector 19.

A light guide fiber not shown in the drawing is inserted into the insertion portion 5, for transmitting illumination light. The base end of the light guide fiber is bent in the control section 6, and fixed to the inside of the light guide connector 11. The distal end of the light guide fiber is fixed to an illumination window 20 provided at the tip 8 of the insertion portion 5.

Furthermore, a connecting male screw portion 11a is provided on the outer periphery of the light guide connector 11. The male screw portion 11a is screwed into a female screw portion formed on the inner periphery of the connecting ring 3c or 24, which is movably provided on the connecting portion 3a of the light guide cable 3 or the connecting portion 12 of the battery-powered light source 4. The connecting ring 3c or 24 is screwed onto and fixed to the connecting portion 3a to integrally connect the endoscope 2 and the light guide cable 3 or the endoscope 2 and the battery-powered light source 4.

Figure 2:
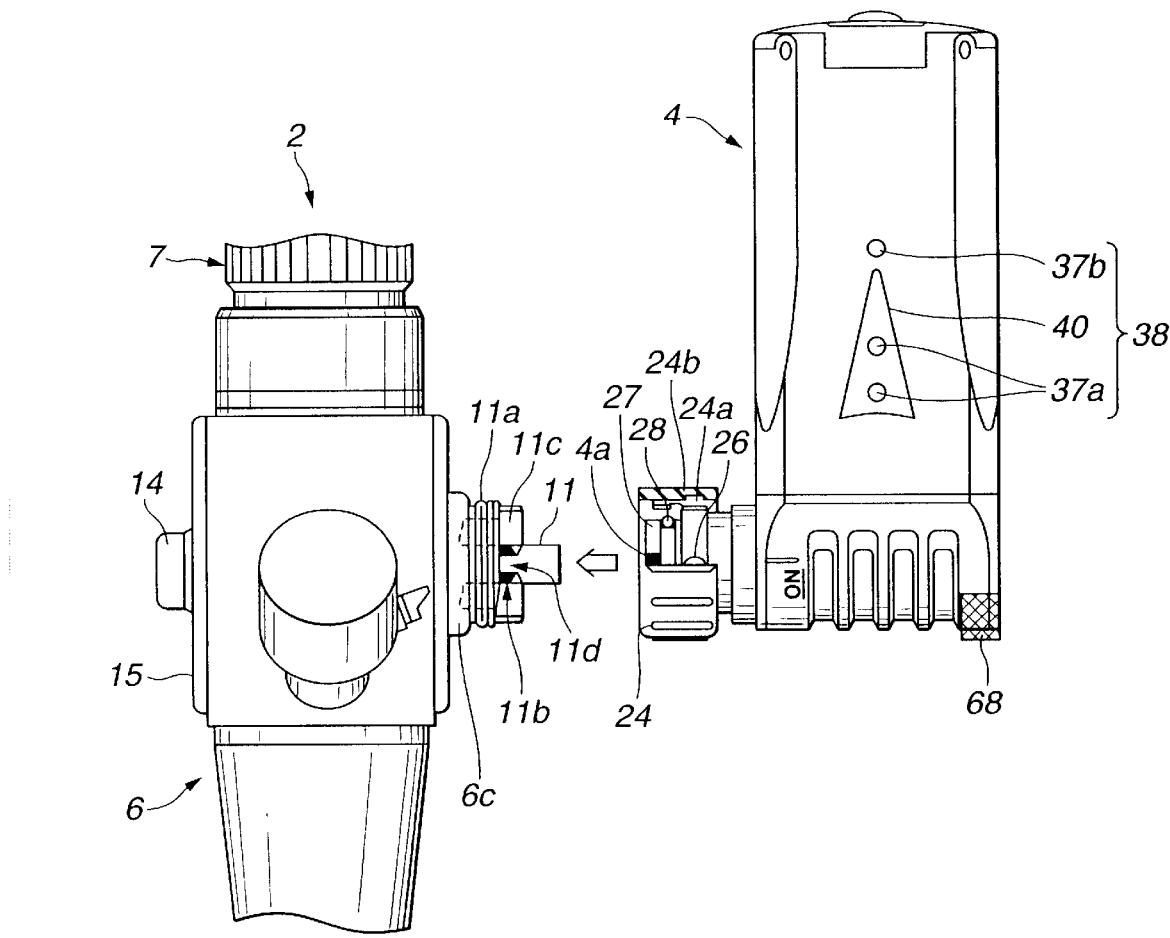
FIG. 2 is a drawing illustrating the appearances of a control section and a connecting portion of an endoscopic battery-powered light source.
Figure 3:
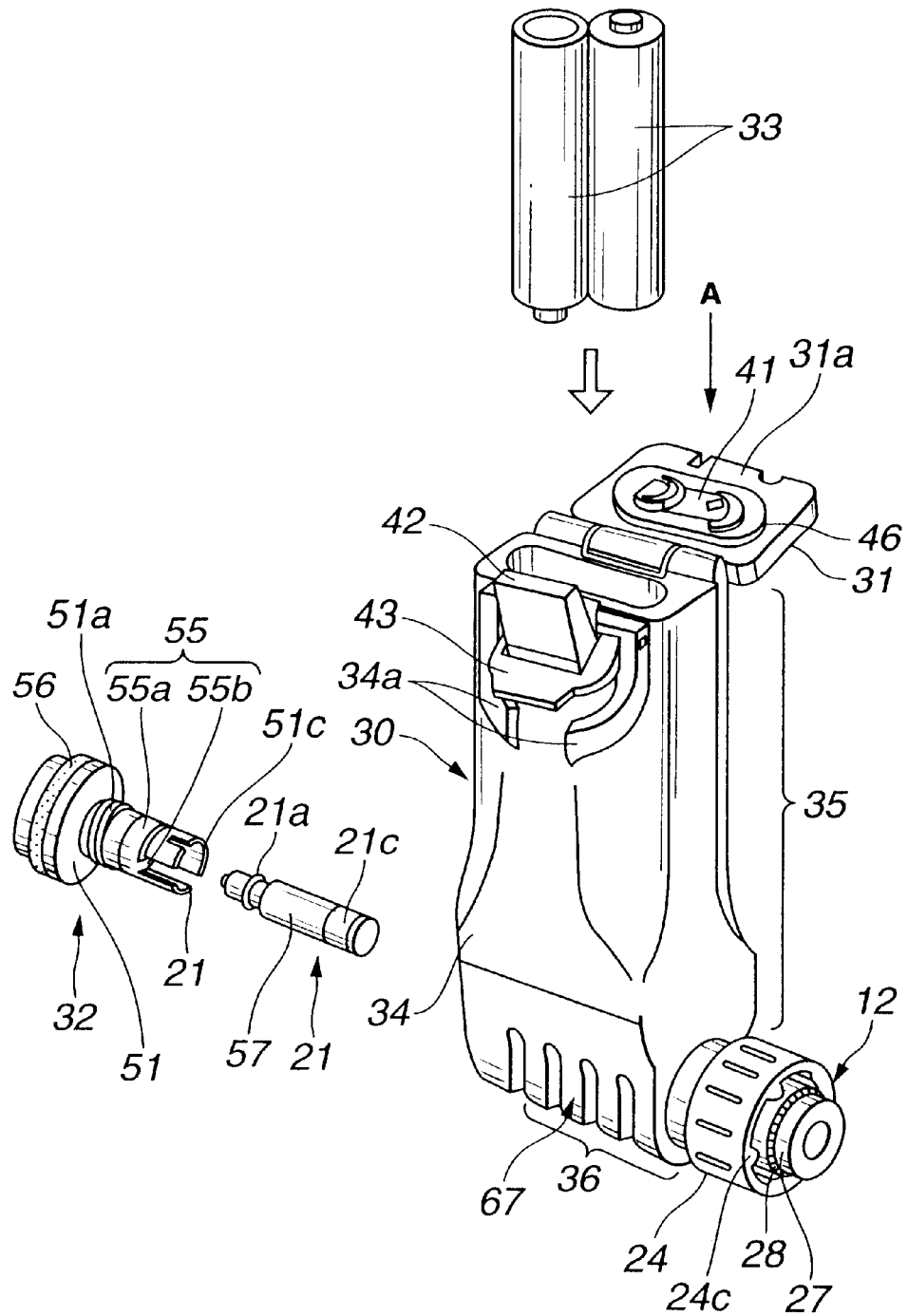
FIG. 3 is a drawing illustrating the whole configuration of an endoscopic battery-powered light source.
Figure 4:
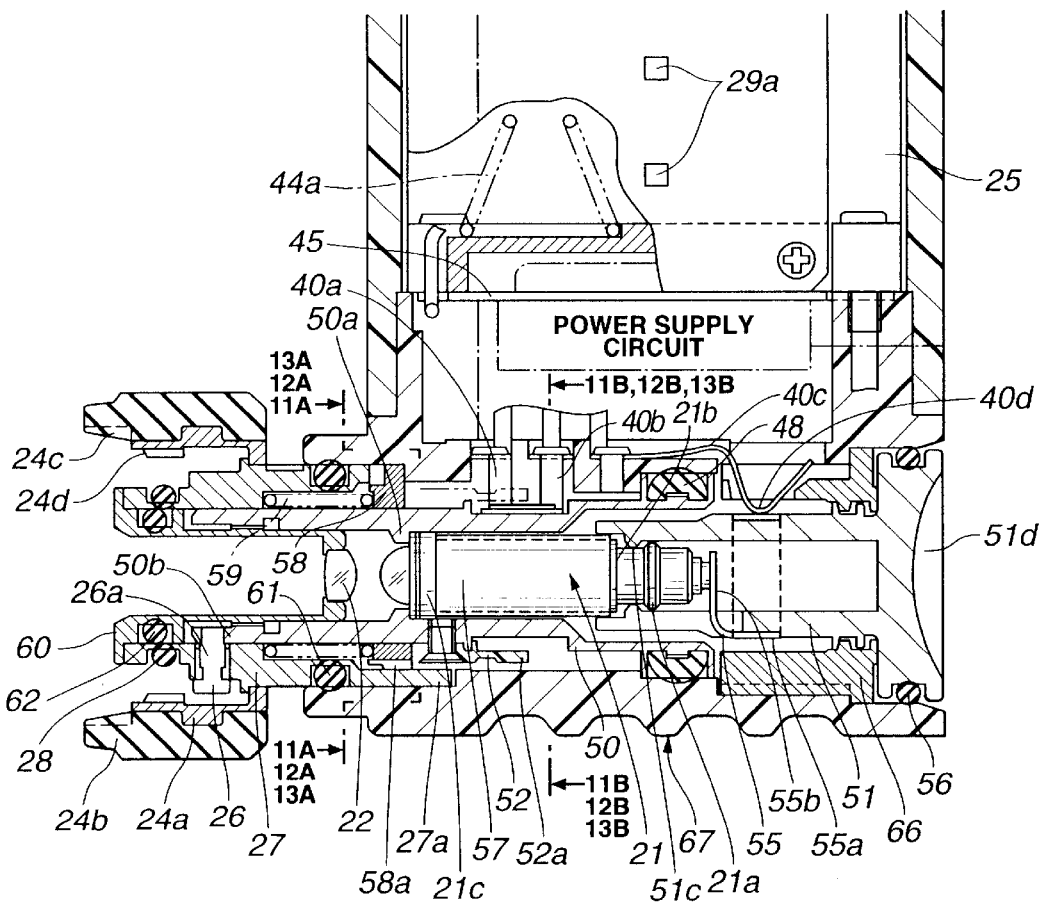
FIG. 4 is a longitudinal sectional view mainly illustrating a lamp room of an endoscopic battery-powered light source.

As shown in FIGS. 2 to 4, the connecting ring 24 of the battery-powered light source 4 comprises a screw main body 24a, and a screw cover 24b. The screw main body 24a has the female screw portion formed therein. The screw cover 24b covers the outer periphery of the screw main body 24a, and is made of a material having elasticity and low thermal conductivity, for example, such as rubber or the like. The tip of the screw cover 24b extends beyond the tip of the screw main body 24a, and has projections 24c integrally formed on the inner periphery thereof.

As shown in FIG. 2, when the battery-powered light source 4 is connected to the endoscope 2, an index 11b provided on a connecting cylinder 11c of the light guide connector 11 is aligned with an index 4a provided on the battery-powdered light source 4 to mount the battery-powered light source 4 on the endoscope 2. By this operation, a positioning pin 26 provided on the battery-powdered light source 4 is inserted into a pin receiving portion lid provided on the connecting cylinder 11c of the light guide connector 11. As a result, the endoscope 2 and the battery-powdered light source 4 are positioned in a predetermined positional relationship therebetween.

In this state, the connecting ring 24 is rotated in a predetermined direction to screw the male screw portion 11a of the light guide connector 11 into the female screw 24d formed on the inner periphery of the screw main body 24a. Consequently, the battery-powered light source 4 is integrally fixed to the endoscope 2. At this time, a water-tight ring 28 provided on a connector 27 on the inner periphery of the connecting ring 24 closely adheres to the inner periphery of the connecting cylinder 11c. Therefore, water tightness in the connecting portion can be secured.

Also, when the above-described screwing engagement is completed, the projections 24c formed on the inner periphery of the screw cover 24b are elastically abutted against the outer periphery of a connector seat 6c projecting from the side of the control section 6. This can form a structure in which the screwing fixed state of the connecting ring 24 and the light guide connector 11 is not easily loosened.

In this structure, only the projections 24c are partially abutted against the connector seat 6c, not the entire surface of the inner periphery of the screw cover 24b, thereby securely completing screwing engagement without strong tightening force. In addition, an unpleasant sound can be prevented from occurring in friction between the screw cover 24b and the connector seat 6c.

In the screw fixing, the battery-powered light source 4 is tuned off so as to turn off an illumination lamp 21. Namely, the positional relationship shown by two-dotted chain lines in FIG. 5 is established, in which the position of a light source main body 30 of the battery-powered light source 4 is parallel to the longitudinal axis direction of the endoscope 2.

Figure 5:
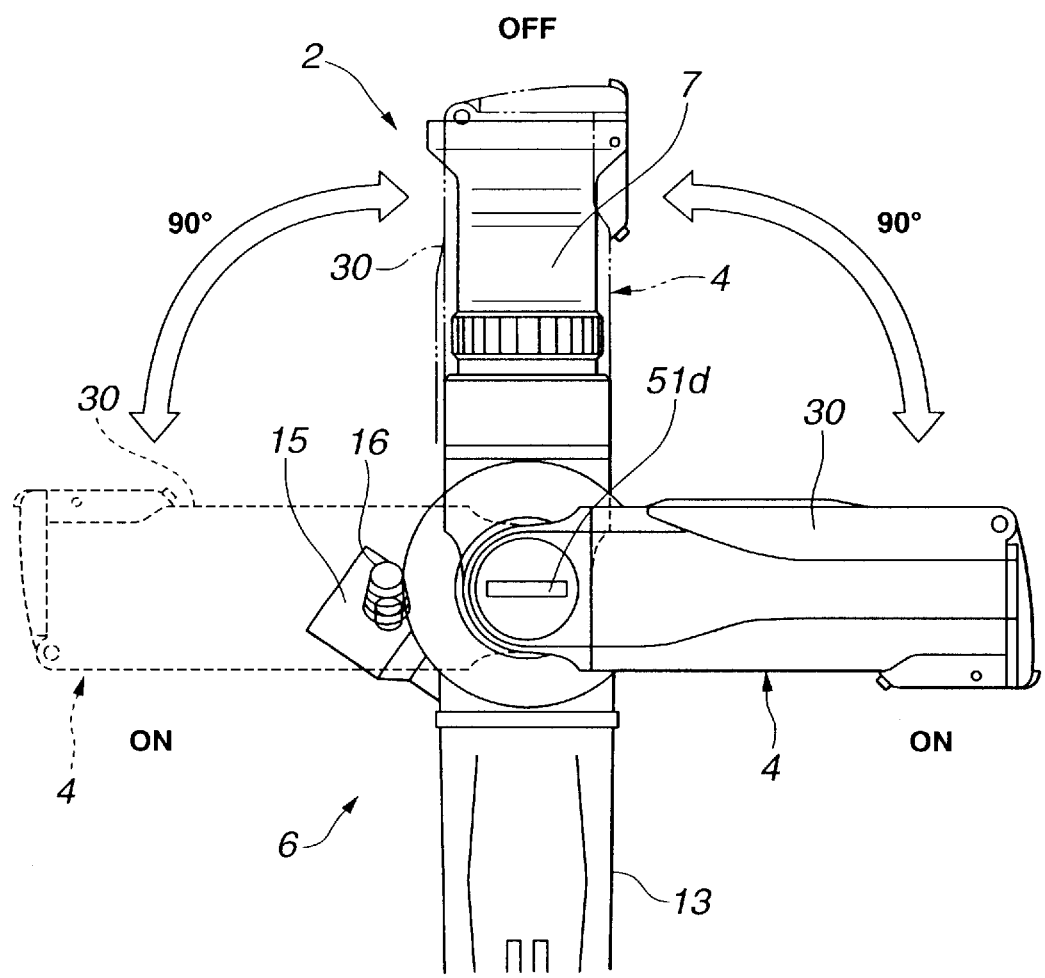
FIG. 5 is a drawing illustrating the switch operation of an endoscopic battery-powered light source due to the difference of the relative positional relation between a control section and the endoscopic battery-powered light source.

When the light source main body 30 is rotated by 90° in the forward or reverse direction based on the OFF position to arrange the light source main body 30 at the position shown by solid lines or broken lines in FIG. 5, turning on the illumination lamp 21.

Therefore, for example, when the battery-powered light source 4 is attached to the light guide connector 11, and the light source main body 30 is arranged at the position shown by the solid lines or broken lines in FIG. 5, the illumination lamp 21 provided in the battery-powered light source 4 is in a light emission state.

The illumination light of the illumination lamp 21 is converged by a converging lens 22 provided in the battery-powered light source 4, and then supplied to the light guide fiber through a light guide cover (not shown in the drawings) made of a transparent glass member and provided at the light incidence end surface of the light guide fiber of the light guide connector 11. The illumination light is transmitted to the distal end through the light guide fiber, and emerges forward from the illumination window 20 to illuminate an inspection site.

On the other hand, the light guide connector 3b provided at the proximal end of the light guide cable 3 shown in FIG. 1 is connected to an existing light source device not shown in the drawing. Therefore, by connecting the light guide connector 3b to the light source device, illumination light emitted from an illumination lamp provided in the light source device is supplied to the light guide fiber of the endoscope 2 through the light guide connector 3b, the light guide fiber in the light guide cable 3, and the connecting portion 3a.

Namely, by connecting the light guide cable 3 to the endoscope 2, the endoscope 2 can be connected to the light source device to perform an endoscopic examination in the same manner as an ordinary endoscope.

The configuration of the battery-powdered light source 4 will be described in detail below.

As shown in FIG. 3, the battery-powered light source 4 comprises the light source main body 30, a cover body 31 connected to the light source main body 30, for example, with a hinge so that it can be freely opened and closed, and a lamp holder 32 serving as a lamp mounting member for holding the illumination lamp 21 which is detachably mounted on the light source main body 30.

By opening the cover body 31, dry batteries 33 can be changed. The illumination lamp 21 can be changed by removing the lamp holder 32 from the light source main body 30. In this embodiment, as the two dry batteries 33 used as the power supply of the battery-powered light source 4, for example, size AA nickel hydride charging batteries are used.

The light source main body 30 mainly comprises an exterior member 34 made of an insulating resin member. The exterior member 34 comprises a battery holding portion 35 for holding the dry batteries 33, and a lamp room 36 for holding the illumination lamp 21.

The battery holding portion 35 comprises a residual amount detector circuit 25 for detecting the residual amount of the dry batteries 33 used. On the basis of the detection result obtained by the residual amount detector circuit 25, a plurality of LEDs 29a and 29b are turned on to inform the operator of the residual amount of the dry batteries 33.

As shown in FIG. 2, a residual amount display portion 38 comprising a plurality of display windows 37a and 37b transmitting light from the LEDs 29a and 29b is provided at a position of the exterior member 34, which corresponds to the LEDs 29a and 29b. In this embodiment, with the dry batteries 33 having a sufficient capacity, the two LEDs 29a which emit green light and which correspond to the display windows 37a are simultaneously turned on.

As the capacity of the dry batteries 33 decreases, the LEDs 29a are turned off one by one. When the residual capacity of the dry batteries 33 is small, the LEDs 29a of green color are switched to the LEDs 29b which emit light of, for example, yellow, and which correspond to the display window 37b. Then, the LEDs 29b are blinked to give the operator a caution about battery shutoff.

In order to improve visibility, a level gauge 40 is provided near the display windows 37a.

An example of display by the LEDs is not limited to the above embodiment, and the color of emitted light and the number of the LEDs may be changed. Besides the display by the LEDs, the capacity may be displayed by, for example, a bar graph using a liquid crystal.

Furthermore, when the cover body 31 is closed after the two dry batteries 33 are contained in the battery holding portion 35, the dry batteries 33 are urged by elastic force of the coil springs 44a and 44b shown in FIG. 16 described later so as to come into contact with an electrically conductive plate 41, to be connected in a series. Therefore, the loading directions of the two dry batteries 33 are opposite to each other.

Figure 6:
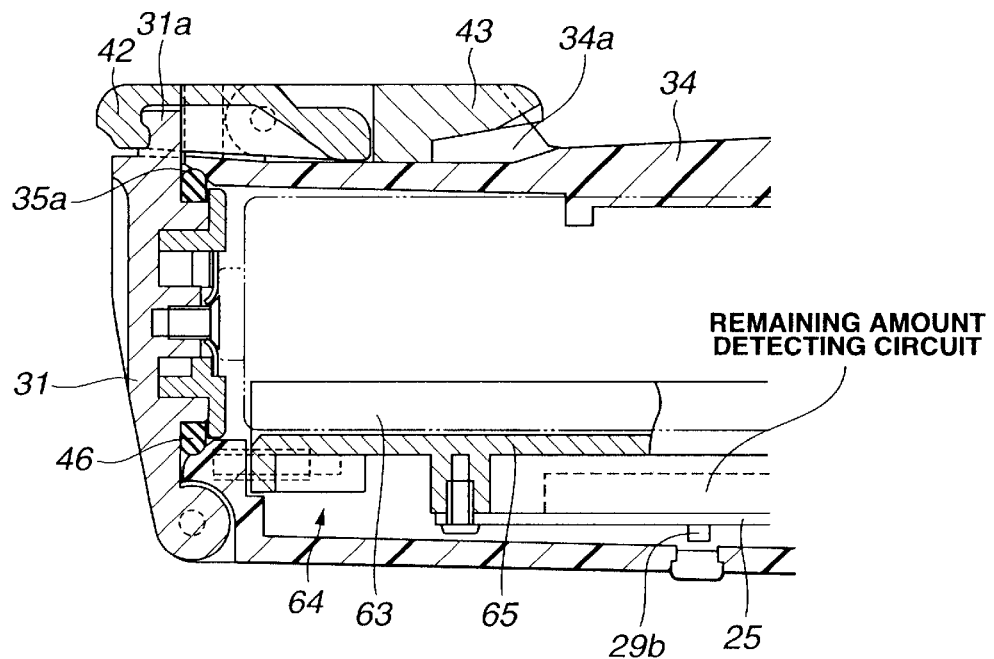
FIG. 6 is a sectional view showing a battery cover and a buckle fixed portion.

As shown in FIGS. 3 and 6, the cover body 31 comprises a fixing claw 31a. On the other hand, the exterior member 34 comprises a lock claw 42 which engages with the fixing claw 31a when the cover body 31 is closed. The lock claw 42 is rotatably provided on an open lever 43 rotatable with respect to the exterior member 34. Therefore, the lock claw 42 is put into an open state or a closed state with respect to the fixing claw 31a in linkage with the operation of the open lever 43. Namely, the cover body 31 is integrally fixed to the light source main body 30 by a so-called buckle-type lock mechanism.

The cover body 31 also has a packing 46 provided on the inner surface thereof. When the cover body 31 is closed, the packing 46 closely adheres to a water-tight surface 35a of the opening of the battery holding portion 35. As a result, the inside of the battery holding portion 35 is kept water-tight.

The water-tight surface 35a is inclined to the direction in which the cover body 31 is closed. Namely, the inclined surface is formed so that the internal dimension of the opening gradually decreases from the opening side to the inner side. This causes the function to generate urging force in the direction to open the cover body 31 to improve the operation of the buckle-type lock mechanism, for example, when the open lever 43 is in a closed state.

In the closed state, the lock claw 42 and the open lever 43 are arranged so as not to cause unevenness in a bank portion 34a integrally provided on the exterior member 34. This can prevent the operation of mistakenly opening the open lever 43 during use or cleaning.

Figure 7:
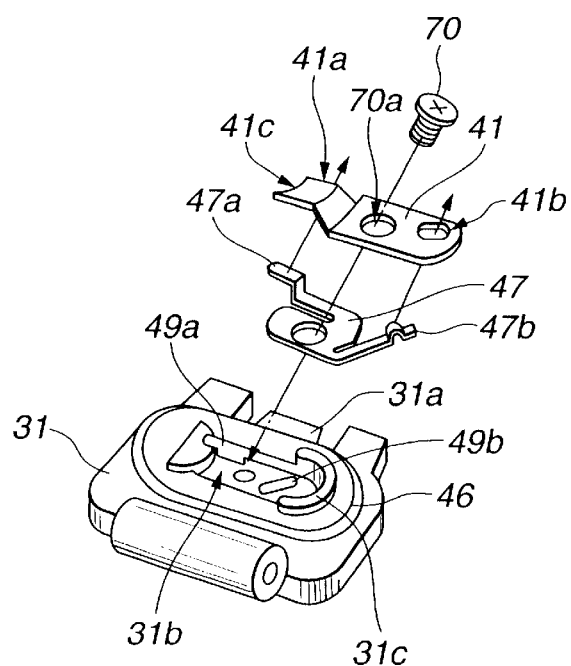
FIG. 7 is an exploded view of a contact member provided on a battery cover.

As shown in FIG. 7, an electrically conductive plate 41 and an electrically conductive panel 47 are fixed to the cover body 31 with a screw 70. The electrically conductive plate 41 is made of a plate material having good conductivity and rigidity and constitutes electrical connection means. The electrically conductive panel 47 is arranged to overlap with the lower side of the electrically conductive plate 41. The electrically conductive panel 47 is made of a plate material having good conductivity and spring elasticity, and has the arms described below, which are abutted on the electrode portions of the dry batteries 33. The cover body 31 comprises a nonconductive member.

Figure 8:
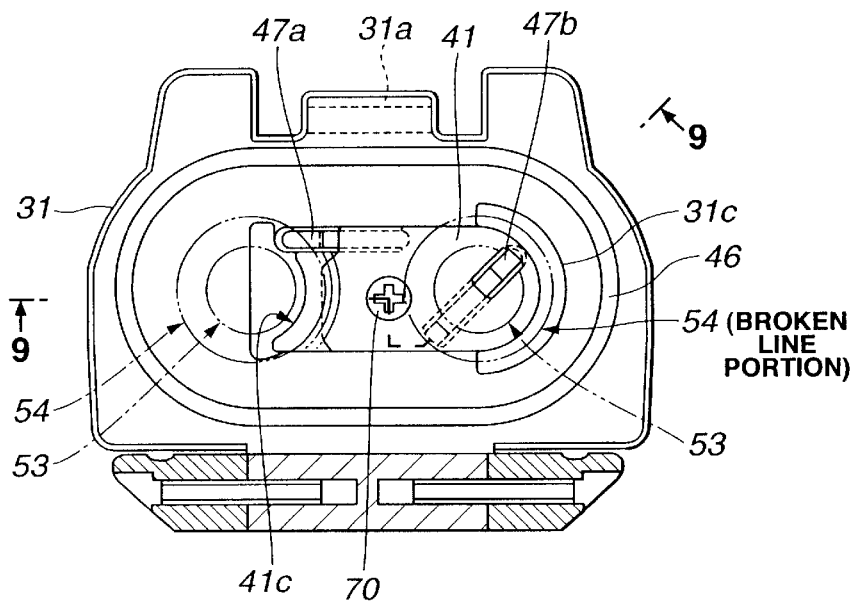
FIG. 8 is a drawing showing the range of both poles of batteries in contact with a battery cover.

As shown in FIGS. 3, 7 and 8, the electrically conductive plate 41 has a stepped end. The stepped end has a half-arc-shaped portion 41c formed so as not to overlap with the region 53 opposed to the anode of one of the dry batteries 33. Also, a notch portion 41a is formed at a predetermined position near the half-arc-shaped portion 41c so that a first elastic arm 47a formed as a thin strip-like elastic contact point in the electrically conductive panel 47 is disposed in the notch portion 41a. The notch portion 41a is overlapped with the region 54 opposed to the cathode of the other dry battery 33.

The electrically conductive plate 41 also has a substantially rectangular opening 41b at the other end opposite the stepped end with a screw hole 70a formed therebetween so that a second elastic arm 47b formed as a thin strip-like elastic contact point in the electrically conductive panel 47 is disposed in the opening 41b.

The electrically conductive panel 47 and the electrically conductive plate 41 are overlapped each other and integrally fixed to the cover body 31 with the screw 70 to arrange the first elastic arm 47a and the second elastic arm 47b in the notch portion 41a and the opening 41b, respectively, of the electrically conductive plate 41.

Figure 9:
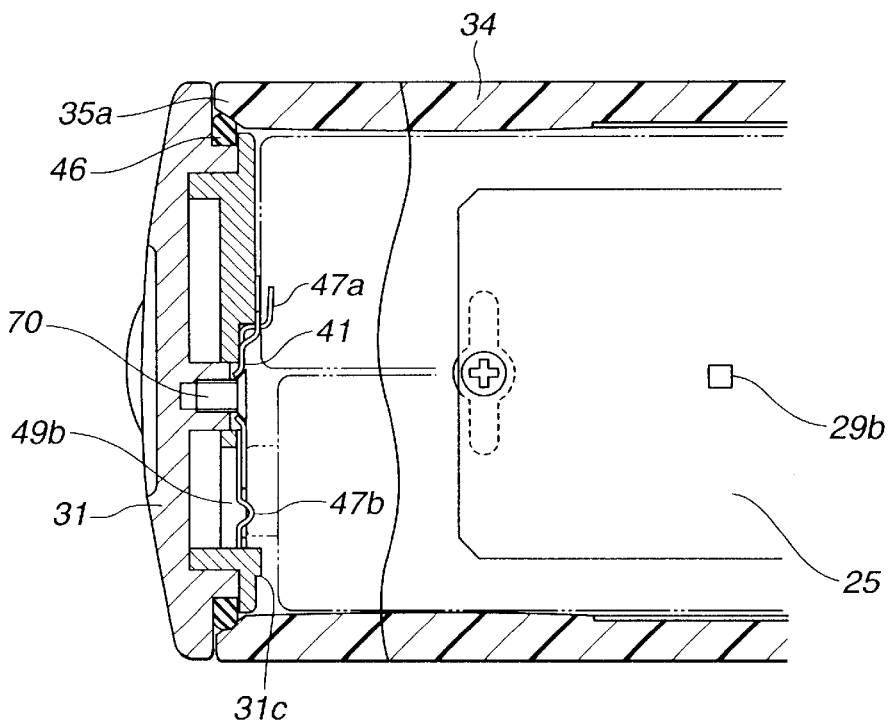
FIG. 9 is a sectional view taken along line IX—IX in FIG. 8.

At this time, the first elastic arm 47a is not overlapped with the region 53 opposed to the anode of one of the batteries 33. Namely, the first elastic arm 47a is located in the region opposed only to the cathode of the other battery 33. As shown in FIG. 9, the points of contact between the arms 47a and 47b and the batteries 33 are located at positions projecting from the upper surface of the electrically conductive plate 41.

The cover body 31 shown in FIG. 7 has a recessed portion 31b formed on the inner side opposed to the dry batteries 33, for positioning and arranging the electrically conductive plate 41 and the electrically conductive plate 47 therein.

Also, relief portions 49a and 49b are formed in the directions in which the elastic arms 47a and 47b are deformed, so that the elastic arms 47a and 47b are elastically deformed when being pressed on the dry batteries 33 in contact therewith.

Furthermore, a substantially C-shaped projection 31c is formed on the inner surface of the side where the opening 41b is arranged so that the anode of one of the batteries 33 passes without contacting the projection 31c, but the cathode cannot pass due to contact with the projection 31c. Therefore, as shown in FIG. 9, the height from the upper surface of the electrically conductive plate 41 to the upper surface of the projection 31c is set to be lower than the projection height of the anode of one of the batteries 33, and the projection of the second elastic arm 47b of the electrically conductive panel 47 is lower than the upper surface of the projection 31c.

The packing 46 is arranged in a substantially oval step formed in the periphery outside the recessed portion 31b.

As shown in FIG. 4, the coil springs 44a and 44b made of a high-conductivity material are arranged at the bottom of the battery holding portion 35 to be connected to a power supply circuit 45, thereby supplying electric power of the dry batteries connected in series to the power supply circuit 45. The power supply circuit 45 is provided with the transformation circuit 39 shown in FIG. 14, for converting the voltage of the dry batteries 33 to the rated voltage of the illumination lamp 21.

Figure 10:
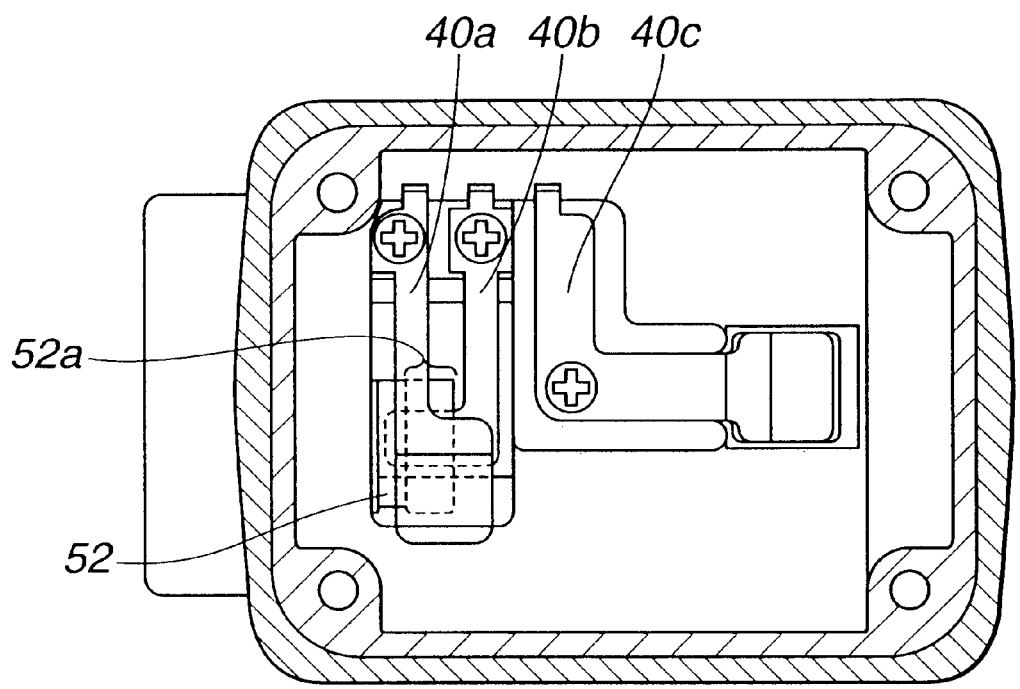
FIG. 10 is a drawing illustrating the shapes and the positional relation of switch contacts.

As shown in FIGS. 4 and 10, electrically conductive contact plates 40a, 40b and 40c having elasticity are arranged between the power supply circuit 45 and the lamp room 36. The electrically conductive contact plate 40a is formed so that an end thereof gets on and off an insulating block 52 within an elastic range by the switching operation described below. As shown in FIG. 11B, with the end of the electrically conductive contact plate 40a getting on the insulating block 52, the electrically conductive contact plates 40b and 40a are separated to establish a switch off state.

Figure 12A:
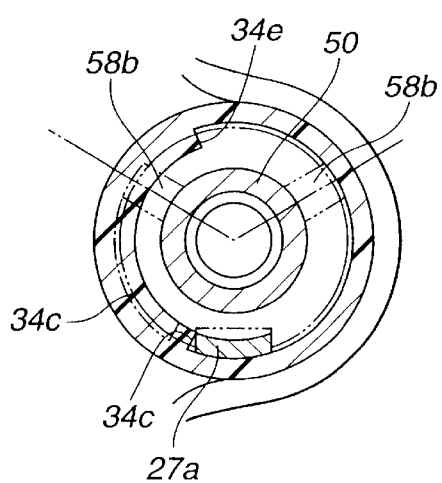
FIG. 12A is a drawing of a sectional view illustrating a positional relationship in a switch ON state, taken along line XIIA—XIIA in FIG. 4.
Figure 12B:
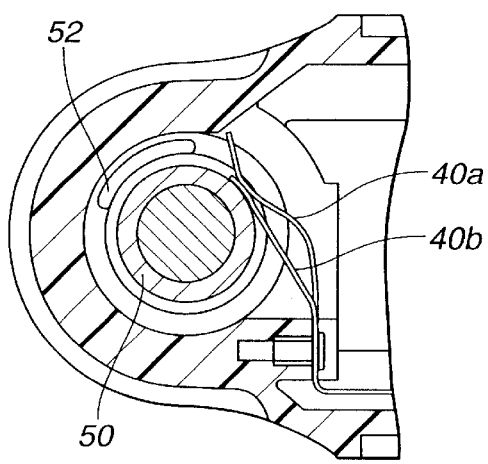
FIG. 12B is a drawing of a sectional view illustrating a positional relationship in a switch ON state, taken along line XIIB—XIIB in FIG. 4.
Figure 13A:
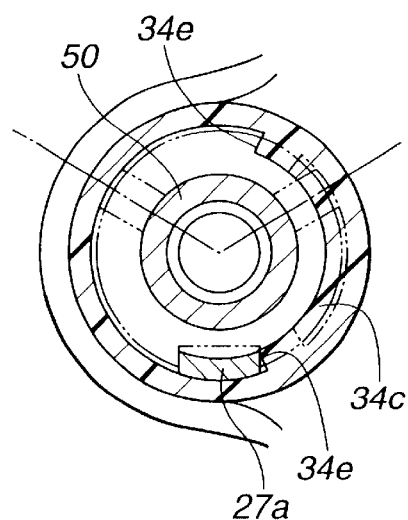
FIG. 13A is a drawing of a sectional view illustrating another positional relationship in a switch ON state, taken along line XIIIA—XIIIA in FIG. 4.
Figure 13B:
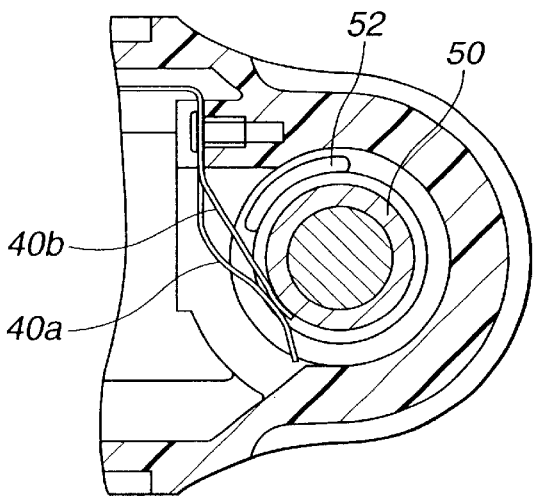
FIG. 13B is a drawing of a sectional view illustrating another positional relationship in a switch ON state, taken along line XIIIB—XIIIB in FIG. 4.

While, with the end of the electrically conductive contact plate 40a getting off the insulating block 52, as shown in FIGS. 12B and 13B, the electrically conductive contact plates 40b and 40a are in pressure contact with each other to establish a switch on state.

In the sliding portion between the electrically conductive contact plate 40a and the insulating block 52, the electrically conductive contact plate 40a has a wide end so as to prevent the insulating block 52 from being cut by the edge of the electrically conductive contact plate 40a. Also, the sliding projection 52a of the insulating block 52 is abutted on a portion of the electrically conductive contact plate 40a nearer to the center thereof, thereby preventing a contact defect due to the occurrence of cutting dust at the contact point. The wide portion of the electrically conductive contact plate 40a also constitutes the portion in contact with the electrically conductive contact plate 40b.

The electrically conductive contact plate 40b is always in pressure contact with a lamp receiving cylinder 50 made of a highly conductive material regardless of the switching operation described below. The electrically conductive contact plate 40b also has a wide end in contact with the lamp receiving cylinder 50 and the electrically conductive contact plate 40a so that in the switch off state, the contact portion partially slips into under the insulating block 52 and is received in the space between the insulating block 52 and the lamp receiving cylinder 50.

The electrically conductive contact plate 40c is arranged so that a bent portion 40d formed by bending the wide end thereof projects into the lamp room 36. When the lamp holder 32 is attached to the lamp room 36, the bent portion 40d is put into pressure contact with a ring-shaped portion 55a of the lamp contact spring 55 provided on the lamp holder 32, as shown in FIG. 4.

Figure 14:
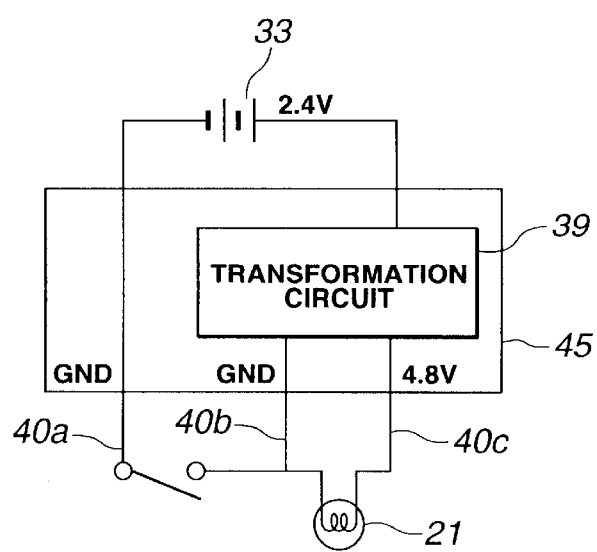
FIG. 14 is a drawing illustrating a power supply circuit of an endoscopic battery-powered light source.

In this embodiment, as shown in FIG. 14, the dry batteries 33 are nickel hydride charging batteries each having an electromotive force of 1.2 V. By connecting the batteries in series, therefore, a power supply voltage of 2.4 V is obtained. The anode side of the dry batteries 33 is connected to the transformation circuit 39, and the cathode side is connected to the electrically conductive contact plate 40a.

On the other hand, the electrically conductive contact plate 40b in contact with the electrically conductive contact plate 40a is connected to a transformation circuit 39 to form a circuit for supplying electric power to the transformation circuit 39 in the state in which the electrically conductive contact plate 40a is in contact with the electrically conductive contact plate 40b. The electrically conductive contact plates 40b and 40c are electrically connected respectively to the electrodes of the illumination lamp 21 with a rated voltage of 4.8 V. The electrically conductive contact plates 40b and 40c constitute output lines of the transformation circuit 39.

Therefore, a circuit is formed, in which when the electrically conductive contact plate 40a is switched to start the transformation circuit 39, the voltage boosted to 4.8 V is supplied to the illumination lamp 21.

The electrically conductive contact plate 40b serves as a ground common to the loop formed by the dry batteries 33 and the transformation circuit 39, and the loop formed by the transformation circuit 39 and the illumination lamp 21.

Also, a short-circuit protecting circuit not shown in the drawing is provided on the power supply circuit 45 so as to detect a voltage drop and stop power supply to the illumination lamp 21 when a maximum current flows through the dry batteries 33 serving as the power supply. In this case, even when the battery-powered light source 4 is switched on, power supply to the illumination lamp 21 is stopped on the circuit.

Furthermore, although not shown in the drawings, the power supply circuit 45 and the remaining amount detecting circuit 25 are connected in an L shape so that the electromotive force of the remaining amount detecting circuit 25 is supplied from the power supply circuit 45.

As shown in FIG. 3, the lamp holder 32 comprises a holder main body 51, a water-tight ring 56, and the lamp contact spring 55. The holder main body 51 comprises a large-diameter portion and a small-diameter portion each made of an insulating material, for example, a resin material. The water-tight ring 56 is disposed on the outer periphery of the large-diameter portion of the holder main body 51. The lamp contact spring 55 has the ring-shaped portion 55a fitted onto the small-diameter portion of the holder body 51, and an arm 55b extending from the ring-shaped portion 55a to be abutted against the base end-side electrode of the illumination lamp 21 with spring elastic force.

The holder main body 51 comprises the male screw portion 51a formed on the outer periphery of the base of the small-diameter portion so as to be screwed into the exterior member 34. The thread of the male screw portion 51a is formed as a so-called trapezoidal screw thread. Therefore, even when the male screw portion 51a is strongly screwed into the exterior member 34, the screw state is prevented from becoming a strong engagement state to permit the lamp holder 32 to be smoothly attached and detached.

Furthermore, a lamp fixing claw 51b is provided at the distal end of the small-diameter portion of the holder main body 51, the lamp fixing claw 51b comprising a plurality of slits provided in a tubular portion. The lamp fixing claw 51b also has a lamp anchoring portion 51c (refer to FIG. 4) is formed on the inner periphery of the end to secure the ring-shaped lamp projection 21a projecting from the outer periphery of the mounting portion of the illumination lamp 21.

The internal diameter of the lamp fixing claw 51b is set to be slightly larger than the outer diameter of the mounting portion of the illumination lamp 21 which is engaged with the lamp fixing claw 51b. The lamp anchoring portion 51c is located between the lamp projection 21a and the stepped portion 21b of the illumination lamp 21 shown in FIG. 3.

Therefore, when the illumination lamp 21 is mounted in the lamp holder 32, the illumination lamp 21 can be freely rotated around the optical axial direction, and can be moved in the optical axial direction.

The arm 55b is disposed behind the lamp anchoring portion 51c to be urged forward by a spring force. Therefore, when the lamp projection 21a is moved beyond the lamp anchoring portion 51c and held thereby, the lamp projection 21a is held to be abutted against the lamp anchoring portion 51c by the urging force of the arm 55b. At this time, the lamp holder 32 is not attached to the exterior member 34.

On the other hand, when force is applied against the urging force of the arm 55b, the lamp projection 21a can be moved to the inner side of the lamp fixing claw 51b.

The outer diameter of the lamp projection 21a is slightly larger than the inner diameter of the lamp anchoring portion 51c, and thus the lamp projection 21a can be pushed in while expanding the lamp anchoring portion 51c. At this time, a feel of click is produced to permit the operator to recognize that the lamp mounting operation is securely performed.

Each of the dimensions is set so that in the mounted state in which the lamp holder 32 holding the illumination lamp 21 is screwed into the exterior member 34, the illumination lamp 21 is abutted against the lamp butting portion 50a formed in the lamp receiving cylinder 50, and the lamp holder 32 is completely screwed, the lamp anchoring portion 51c is received in the space between the lamp projection 21a and the stepped portion 21b within the range in which the lamp holder 32 of the illumination lamp 21 can be moved in the optical axial direction.

Also, the lamp projection 21a of the illumination lamp 21 is engaged with the lamp anchoring portion 51c by a force stronger than the spring force of the lamp contact spring 55.

Furthermore, the arm 55b of the lamp contact spring 55 extends to substantially the center of the holder main body 51 through the slits of the lamp fixing claw 51b. When the illumination lamp 21 is mounted in the lamp holder 32, the arm 55b is elastically abutted against one of the electrodes at the bottom of the illumination lamp 21.

Also, as shown in FIG. 4, a groove 51d is formed at the base end of the holder main body 51 so that the tip of a minus driver or a coin is fitted therein. By fitting the coin or the like into the groove 51d, the holder main body 51 can be attached and detached by rotating the holder main body 51.

When the lamp holder 32 is screwed into the exterior member 34, water tightness of the inside of the battery-powered light source 4 is maintained by the water-tight ring 56.

The outer periphery of the metal tube 21c of illumination lamp 21, which constitutes one of the electrodes, is coated with an electrically nonconductive resin tube 57 having low thermal conductivity so that the front end portion of the lamp 21 is exposed.

FIG. 4 is a sectional view of the lamp room 36 in which the lamp holder 32 with the illumination lamp 21 attached thereto is mounted on the battery-powdered light source 4. FIG. 4 shows the state in which the illumination lamp 21 is turned on. In this embodiment, the switch ON positions include two positions including the states shown in FIG. 12B and FIG. 13B, which are sectional views taken along C—C in FIG. 4. These states respectively have the positional relationships shown by solid lines and broken lines in FIG. 5 showing the whole construction.

In the ON state, the exterior member 34 is rotated by 90° in each of the forward and reverse directions with respect to the lamp receiving cylinder 50 described below to establish the switch OFF state shown in FIG. 11B in which the illumination lamp 21 is turned off.

The lamp receiving cylinder 50, substantially cylindrical, made of a material having good conductivity is disposed in the lamp room 36. The base end of the lamp receiving cylinder 50 is formed in a flange shape, and is rotatably provided in the exterior member 34 with an elastic ring 48 provided at the base end increase sliding resistance.

An insulating block 52, which elastically deforms the electrically conductive contact plate 40a, is fixed at a predetermined position of the lamp receiving cylinder 50. The fixing position corresponds to the switch position where the illumination lamp 21 is turned on or off.

The inner hole at substantially the center of the lamp receiving cylinder 50 is formed with a dimension which causes the outer periphery of the cylinder 21c of the illumination lamp 21 to be fitted into the hole. A lamp abutting portion 50a is formed at the predetermined position of the inner periphery near the end of the lamp receiving cylinder 50 so as to function as a positioning portion in contact with the peripheral portion at the front end of the cylinder 21c of the illumination lamp 21. The cylinder 21c functions as an electrode opposite the other electrode provided at the bottom of the illumination lamp 21.

Figure 15:
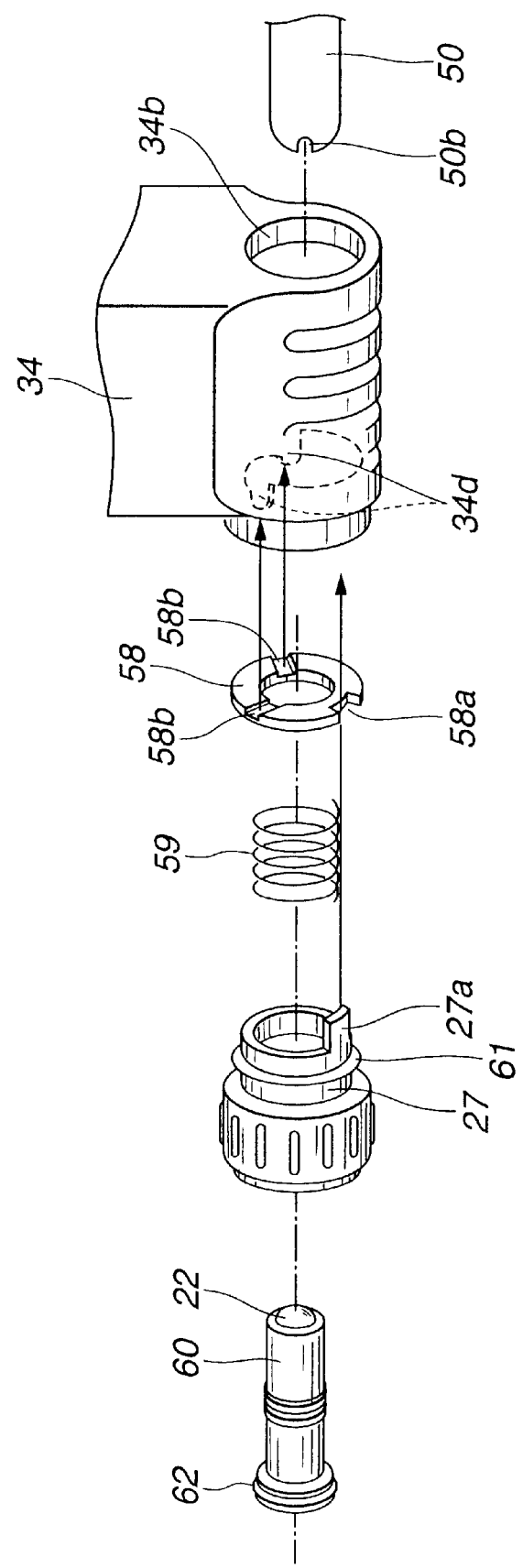
FIG. 15 is an exploded view of the components of a click mechanism.

As shown in FIG. 15, a disk-shaped click plate 58, a spring 59 and the connector 27, which constitute the click mechanical portion, are successively fitted onto the periphery of an end of the lamp receiving cylinder 50 from an opening opposite a lamp holder mounting port 34b of the exterior member 34. The lamp receiving cylinder 50 is inserted into the lamp holder mounting part 34b.

The connector 27 has a positioning pin 26 screwed into the connector 27 to project from the inner periphery thereof (refer to FIG. 4). Therefore, a projecting portion 26a of the positioning pin 26 is engaged in a notch portion 50b provided at the end of the lamp receiving cylinder 50 to fit the connector 27 into the lamp receiving cylinder 50.

The click plate 58 has a substantially U-shaped slit 58a formed therein. A rotation regulating portion 27a formed by extending a portion of the periphery of the connector 27 from the base end side is passed through the slit 58a.

Furthermore, a lens holding cylinder 60 comprising a cylindrical hollow into which the light guide connector 11 of the endoscope 2 is inserted, and the converging lens 22 fixed to the bottom of the cylindrical hollow with an adhesive in a water-tight manner is screwed into the lamp receiving cylinder 50 to integrally fix the connector 27 to the lamp receiving cylinder 50.

Furthermore, a nonconductive female screw block 66 to be screwed onto the male screw portion 51a of the holder main body 51 is fitted into the lamp holder mounting port 34b. Also, a water-tight ring 61 is provided on the base end side of the connector 27 fitted into the exterior member 34 to form a water-tight structure. A water-tight ring 62 is also fitted on the outer periphery of the end of the lens holding cylinder 60 to secure water tightness.

Figure 11A:
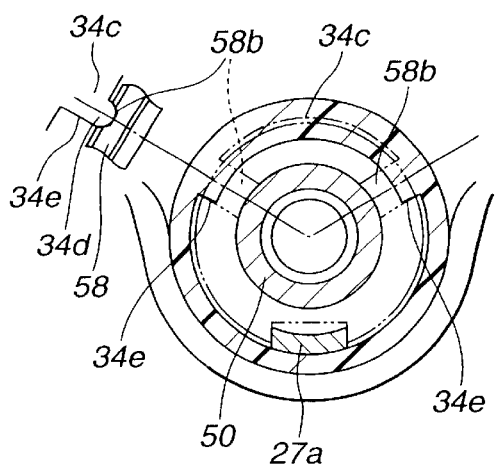
FIG. 11A is a drawing of a sectional view illustrating the positional relationship in a switch OFF state, taken along line XIA—XIA in FIG. 4.
Figure 11B:
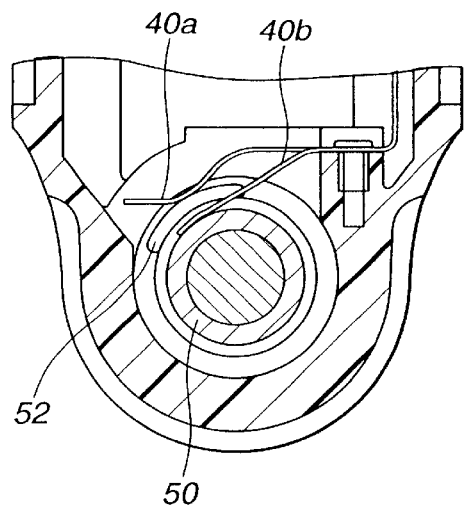
FIG. 11B is a drawing of a sectional view illustrating the positional relationship in a switch OFF state, taken along line XIB—XIB in FIG. 4.

In this state, the click plate 58 is always urged to the projections 34d provided at two positions of an internal peripheral stepped portion 34c of the exterior member 34 (refer to FIGS. 15 and 11A).

The click plate 58 can be moved against the urging force of the spring 59. The click plate 58 also has grooves 58b formed at the same angular positions as the projections 34d. By a switching operation, the projections 34d are fitted into the grooves 58b to produce a feel of click (refer to FIG. 11A).

The stepped portion 34c is formed for changing the insertion depth of the connector 27 within a predetermined angular range. As shown in FIG. 11A, both sides of the step projecting along the inner periphery serve as rotation stoppers 34e in contact with the rotation regulating portion 27a.

In the above-described structure, a click fixing position is provided so that the exterior member 34 is rotated with respect to the lamp receiving cylinder 50 within a predetermined angular range, and held at a predetermined relative position with a feel of click within the angular range.

In this embodiment, this click fixing position is the switch OFF position, and the exterior member 34 is rotated in the range of 90° from this OFF switch position in each of the forward and reverse directions to be moved to the switch ON position as the regulating position. The rotation angle can be appropriately changed.

The exterior member 34 has a concavoconvex portion 67 formed in the outer periphery thereof around the lamp room 36, for increasing the area of contact with air. The concavoconvex portion 67 can effectively discharge the heat generated from the illumination lamp 21 to the outside of the exterior member 34.

Figure 16:
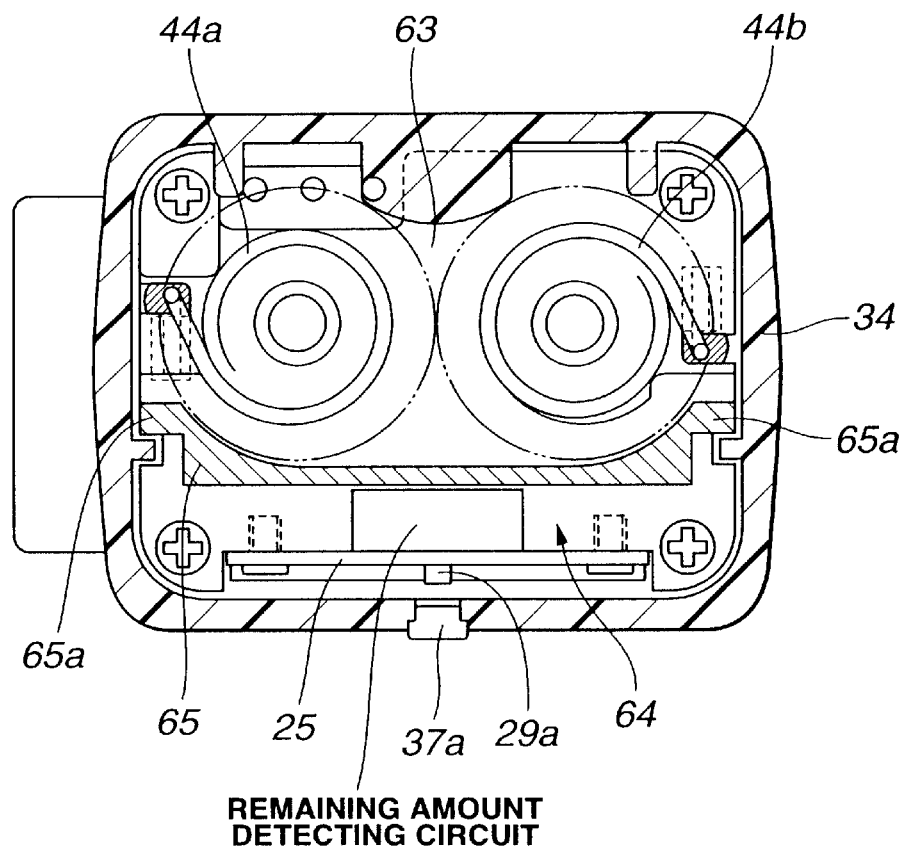
FIG. 16 is a drawing of a sectional view illustrating a partition member for partitioning a substrate containing room.

As shown in FIGS. 6 and 16, the space for a substrate receiving room 64 in which a substrate comprising the remaining amount detecting circuit 25 and the power supply circuit 45 is arranged is separated from the space for the battery room 63, which contains the dry batteries 33, by a partition member 65 comprising a nonconductive member.

The partition member 65 has a rib-form rim 65a thereof so that the rib is engaged with the exterior member 34 without a space therebetween. It is thus possible to prevent foreign materials from entering the substrate receiving room 64 from the battery room 63, and prevent a defect such as a short circuit or the like due to the entrance of conductive foreign materials. The partition member 65 has the function to maintain and fix the remaining amount detecting circuit 25.

A description will now be made on the function of the battery-powered light source 4 of this embodiment.

As shown in FIG. 3, the cover body 31 of the light source main body 30 is opened, the two dry batteries 33 are contained in the battery receiving portion 35 so that the polarities are opposite to each other, and then the cover body 31 is closed. Then, the lock claw 42 is engaged with the fixing claw 31a of the cover body 31 by moving the open lever 43, and the open laver 43 is pushed down toward the side of the exterior member 34 to fix the cover body 31 by the lock claw 42 in such a manner that the cover body 31 is pulled toward the light source main body 31.

As a result, a packing 46 provided on the cover body 31 closely adheres to the opening of the battery receiving portion 35 to establish the water-tight state. The conductive plate 41 and the conductive spring 47 provided on the cover body 31 are brought into contact with the opposite electrodes of the dry batteries 33 to connect the two dry batteries 33 in series. At this time, both poles of the dry batteries 33 are held with urging force between the coil springs 44a and 44b in the battery holding portion 35 and elastic arms 47a and 47b of the cover body 31.

Next, the base end side of the illumination lamp 21 is inserted into a lamp fixing claw 51b of the lamp holder 32. At this time, a projection 21a of an illumination lamp 21 is fitted into the lamp fixing claw 51b while pressing a lamp anchoring portion 51c formed on the inner periphery of the lamp fixing claw 51b to pass beyond the lamp anchoring portion 51c. This establishes the fixed state with a feel of click.

At the same time, an arm 55b of a lamp contact spring 55 is elastically abutted against the base end electrode of the illumination lamp 21. In this state, the illumination lamp 21 can be moved around the optical axis with respect to the lamp holder 32, and can be moved against the elastic force of the lamp contact spring 55 in the optical axial direction.

Next, a coin or the like is fitted into a groove 51d of the lamp holder 32, and then rotated to screw a male screw portion 51a of the lamp holder 32 into the female screw portion of the exterior member 34. Consequently, the illumination lamp 21 is mounted in the lamp room 36 of the light source main body 30.

Before the lamp holder 32 is completely screwed into the exterior member 34, the peripheral portion at the distal end of the illumination lamp 21, which functions as the other electrode, is abutted against the positioning lamp abutting portion 50a provided on the lamp receiving cylinder 50 and positioned. Namely, the lamp holder 32 is screwed into the exterior member 34 with the lamp projection 21a being abutted against the lamp anchoring portion 51c.

Therefore, the illumination lamp 21 is abutted against the lamp abutting portion 50a in the initial stage of screwing engagement, and when the base end electrode of the illumination lamp 21 is then moved to the inside of the lamp fixing claw 51b to elastically deform the arm 55b, screwing engagement is completed to establish the mounted state shown in FIG. 4.

The lamp anchoring portion 50a has the function to position the illumination lamp 21 at a position where the light emitted from the illumination lamp 21 is converged with highest efficiency to the incidence end of the light guide fiber of the endoscope 2.

At the same time, the holder main body 51 is integrally fixed to the exterior member 34, and the electrically conductive contact plate 40c connected to the output side of the transformation circuit 39 is put into elastic contact with the ring-shaped portion 55a of the lamp contact spring 55, as shown in FIG. 4.

Furthermore, the inside of the lamp room 36 in which the illumination lamp 21 is mounted is put into a water-tight state by a water-tight ring 56.

Then, the connecting portion 12 of the battery-powered light source 4 is connected to the light guide connector 11 of the endoscope 2. As a result, the lamp receiving cylinder 50 integrated with the connecting portion 12 is integrally fixed to the light guide connector 11.

At the position shown by the one dotted chain lines in FIG. 5, a lamp lighting switch is turned off. In this state, as shown in FIG. 11B, the electrically conductive contact plate 40a rides on an insulating block 52 to separate the electrically conductive contact plate 40a from the electrically conductive contact plate 40b, thereby stopping the operation of the transformation circuit 39. Namely, the illumination lamp 21 is not turned on. In addition, with the lamp turned off, electric power is not supplied to the remaining amount detecting circuit 25, and thus the remaining amount is not displayed in the remaining amount display portion 38.

Furthermore, in the off state, the rotation regulating portion 27a of the connector 27 is at an intermediate position between the rotation stoppers 34e, as shown in FIG. 11A. At this time, the click plate 58 is at the position where grooves 58b are engaged with the projections 34d. Namely, the click mechanical portion exhibits a holding function, and the switch OFF function is assigned to this holding state.

Next, the light source main body 30 is rotated with respect to the control section 6 to the position shown by the solid lines or broken lines in FIG. 5. In this case, the rotation direction in which the remaining amount display portion 38 faces the eyepiece 7 side is considered as the forward direction. The rotation range of the exterior member 34 which is rotated around the lamp receiving cylinder 50 as the axis is determined by the rotation stoppers 34e abutted against the rotation regulating portion 27a, as shown in FIG. 12. In this embodiment, the rotation range is set to an angle of about 90° from the OFF position.

In the operation of rotation from the OFF position, the projections 34d located in the grooves 58b of the click plate 58 must be operated such that the projections 34d go over the grooves 58b against the elastic force of the spring 59. Therefore, a large amount of rotating force is required for the initial stage of movement from the OFF position. However, after the projections 34d are removed from the grooves 58b, the rotating operation can be performed by a constant and stable amount of rotating force smaller than that in the initial stage of movement.

Furthermore, the amount of force for click fixing can be appropriately controlled by changing the amount of force of the spring 59 for pressing the click plate 58, or changing the form of engagement between the grooves 58b and the projections 34d.

Furthermore, in order to prevent friction between the click plate 58 and the sliding projections 34d, a coating may be provided on the surface of the click plate 58, for improving slippage.

As shown in FIG. 12B, in the ON state in the forward direction, the electrically conductive contact plate 40a is come down from the insulating block 52, and put into contact with the electrically conductive contact plate 40b. In this state, electric power is supplied from the dry batteries 33 to the transformation circuit 39 to supply electric power boosted to the rated voltage of the illumination lamp 21. Namely, a closed circuit comprising the transformation circuit 39, the electrically conductive contact plate 40c, the lamp contact spring 55, the illumination lamp 21, the lamp receiving cylinder 50, the electrically conductive contact plate 40b and the transformation circuit 39 is formed to turn on the illumination lamp 21.

At the same time as the illumination lamp 21 is turned on, the remaining amount detecting circuit 25 is started to monitor the output voltage value of the dry batteries 33, or the like, and the remaining amount of the batteries is calculated from the voltage value and displayed on the remaining amount display portion 38 at any time.

The illumination light emitted from the illumination lamp 21 is converged by the converging lens 22, and is efficiently entered on the light guide fiber disposed on the light guide connector 11 of the endoscope 2. The illumination light entered on the light guide fiber is transmitted to the distal end and emerges from the front side through the illumination window 20 to illuminate a subject such as an affected area in a body cavity of a living body in which the insertion portion 5 is inserted.

On the other hand, an optical image of the subject illuminated with the illumination light is formed at the distal end of an image guide fiber by an objective lens 23, and transmitted to the base end side. The image can be observed through the eyepiece portion 7 to perform endoscopic diagnosis of the affected area or the like.

At this time, the heat generated during lighting of the illumination lamp 21 is transmitted to the lamp receiving cylinder 50, and further transmitted to the light guide connector 11 of the endoscope 2 through the connecting portion 12. Then, the heat diffuses to the metal parts in the control section 6 from the light guide connector 11.

In order to further improve the efficiency of light convergence, the glass sphere of the illumination lamp 21 may be formed in a thickness corresponding to a lens so that the light emitted from the illumination lamp 21 is made closer to a spot light beam.

In this way, in this embodiment, the illumination lamp 21 which is a source of heat generation, is contained in the lamp receiving cylinder 50 made of a conductive metal member, thereby positively diffusing excess heat generated from the illumination lamp 21 to the inside of the endoscope main body through the lamp receiving cylinder 50.

Furthermore, an air layer is provided between the lamp receiving cylinder 50 and the exterior member 34 to avoid heat from being transmitted directly to the exterior member 34.

Furthermore, even when heat is transmitted to the exterior member 34 around the lamp room 36 in use for a long time, the heat is efficiently released to the air through the concavoconvex portion 67.

In addition, the lamp holder 32 in which the illumination lamp 21 is mounted comprises the holder main body 51 made of a resin member with low thermal conductivity, and thus the outer surface in which the groove 51d is exposed is not heated to a high temperature. Therefore, the surface of the exterior member 34 around the lamp room 36, which is brought into contact with the operator's hand, is prevented from being heated to a high temperature which inhibits use.

Therefore, heat is not stored in the inside, thereby preventing an adverse effect of heat on the internal electric circuit or the like.

In addition, the screw cover 24b of the connecting ring 24 is made of a rubber material with low thermal conductivity, thereby preventing heat transmittance to the operator's hand.

After observation is completed, when the light source main body 30 is rotated to the OFF position, the light source main body 30 is positioned and fixed at the OFF position by the click mechanism, and at the same time, the electrically conductive contact plate 40a rides on the insulating block 52 to simultaneously turn off the illumination lamp 21 and the remaining amount display portion 38.

In the above-described ON/OFF rotating operation, the lamp holder 32 is also rotated together with the exterior member 34, while the illumination lamp 21 is not rotated because of the great sliding resistance between the illumination lamp 21 and the lamp receiving cylinder 50 due to engagement with the lamp holder 32.

Also, at the same time, the rotating force transmitted from the illumination lamp 21 to the lamp holder 32 is small.

Therefore, even when the ON and OFF operations are repeated, the screwing engagement between the lamp holder 32 and the exterior member 34 is not loosened.

Furthermore, the connecting ring 24 for fixing the light guide connector 11 and the connector 27 is screwed onto the male screw portion 11a with the screw cover 24b elastically adhered to the connector base 6c of the control section 6. Therefore, even when the ON/OFF operations are repeated, the screwing engagement is not loosened.

On the other hand, the light source main body 30 can be rotated with respect to the endoscope 2, for example, in the direction reverse to the above-described direction to be located at the position shown by the broken lines in FIG. 5, establishing a second lamp ON state.

At this time, the rotation range of the exterior member 34 rotated around the lamp receiving cylinder 50 is determined by the rotation regulation portion 27a and the rotation stoppers 34e abutted against the rotation regulation portion 27a. The rotation range is set to an angle of about 90° from the switch OFF position.

Therefore, the rotational angle of the light source main body 30 with respect to the control section 6 of the endoscope 2 is 90° from the switch OFF position at the center in each of the forward and reverse directions. Namely, the total rotation angle is 180°.

In the reverse rotation, the state of contact between the electrically conductive contact plates 40a and 40b is as shown in FIG. 13B. The switch operating mechanism in the reverse direction is different only in the rotational direction from the above-described switch operating mechanism in the forward direction, and the configuration of both mechanisms are the same. Therefore, a description of the reverse switching operation is omitted.

The click-fixed switch OFF position and the above-described total rotation angle can be appropriately changed by changing the angle formed by the stepped portion 34c and the positions of the grooves 58b of the click plate 58.

Furthermore, a plurality of click fixing positions can be set in the range of the total rotation angle by changing the numbers and the positions of the stepped portions 34c and the grooves 58b. Also, a plurality of predetermined switch functions may be assigned to the click fixing positions.

Figure 17:
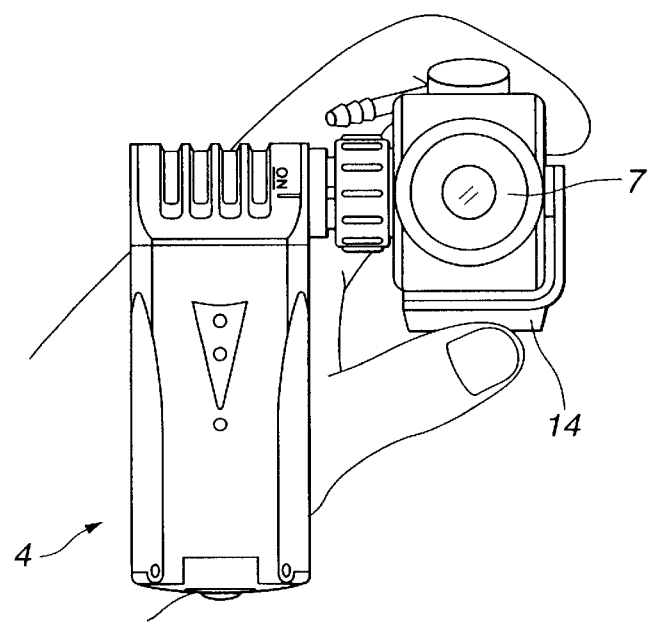
FIG. 17 is a drawing showing an example of a method of gripping an endoscope.
Figure 18:
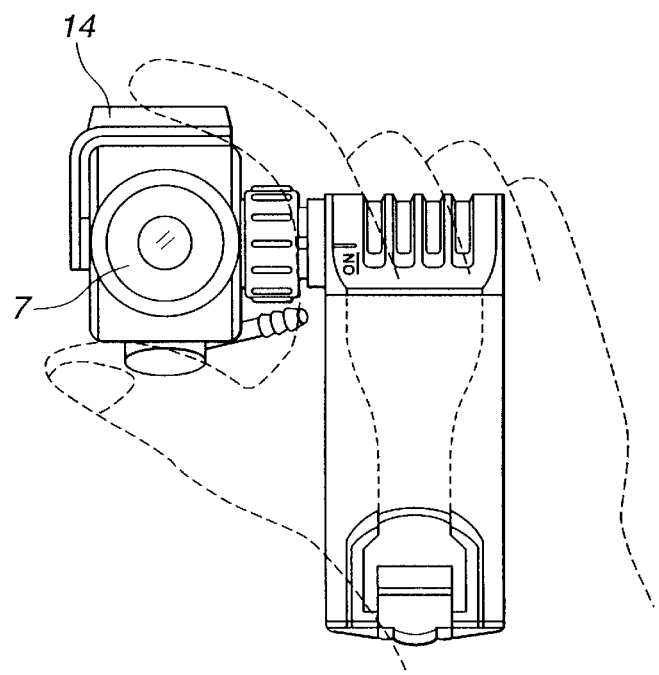
FIG. 18 is a drawing showing another example of a method of gripping an endoscope.

The battery-powered light source 4 having the above two switch ON positions and switch OFF position can be gripped and operated by two methods, as shown in FIGS. 17 and 18.

Figure 19A:
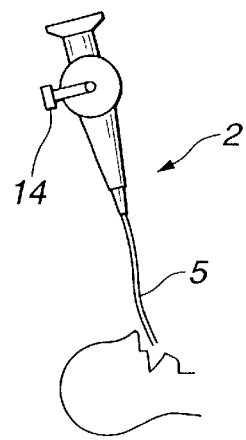
FIG. 19A is a drawing illustrating the state in which an endoscope is used for a patient lying down.
Figure 19B:
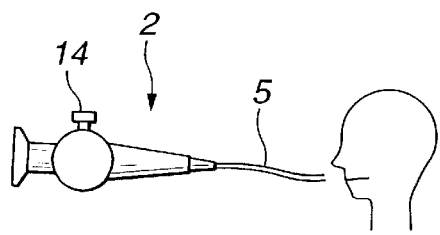
FIG. 19B is a drawing illustrating the state in which an endoscope is used for a patent facing an operator.
Figure 19C:
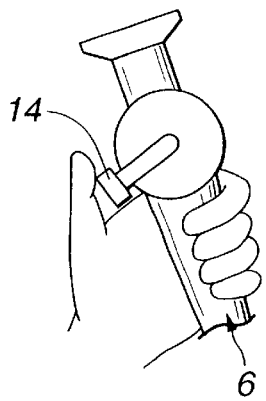
FIG. 19C is a drawing showing a further example of a method of gripping an endoscope.

In use for a patient lying down as shown in FIG. 19A, the control section 6 is gripped with the palm of the operator's hand, and the bending operation lever 14 is generally operated with the operator's thumb, as shown in FIG. 19C. Therefore, as shown in FIG. 17, the light source main body 30 is rotated in the forward direction to turn on the illumination lamp 21 in the state shown in the solid lines in FIG. 5. In this state, the light source can be most naturally gripped for operation and observation with the insertion portion 5 facing downward.

On the other hand, in use for a patient facing the operator as shown in FIG. 19B, the insertion portion 5 must be in a substantially horizontal state for performing operation and observation. In this case, the gripping method shown in FIG. 19C makes it unnatural and difficult to operate the bending operation lever 14 with the operator's thumb with the insertion portion set in the horizontal state.

Therefore, in this case, the light source main body 30 is moved to the position shown by the broken lines in FIG. 5 by rotating it in the reverse direction to turn on the illumination lamp 21. At the same time, the control section 6 is reversed to turn the bending operation lever 14 upward, and in this state, the endoscope 2 is gripped as shown in FIG. 18. Namely, the battery-powered light source 4 is gripped with the operator's palm so as to wrap the battery-powered light source 4 therein, and the bending operation lever 14 is operated with the operator's forefinger. By this gripping method, the light source main body 30 can be securely gripped with the operator's palm, and the curved operating lever 14 can be naturally operated with the operator's forefinger, thereby improving operability.

The switch OFF position is a position at which the light source main body 30 is parallel to the control section 6 in order to facilitate storage of the endoscope 2 in a storage place with the battery-powered light source 4 being attached thereto.

In this way, besides the regulated positions, the arrangement positions of the battery-powered light source related to the control section of the endoscope are provided at intermediate positions within the whole rotational range, and the desired switch function is assigned to each of the arrangement positions. Therefore, the battery-powered light source can be positioned and held at each of the switch positions, thereby significantly improving the operability and usability of the endoscope.

Therefore, in an endoscope apparatus in which a switch operation is performed by changing the relative position of the battery-powered light source connected to the control section of the endoscope, a plurality of switch positions are provided in a range in which the relative position is changed, and a click mechanism functions at each of the switch positions, thereby facilitating and securing switching of a plurality of switches. In addition, in consideration of operation conditions, the relative position of the battery-powered light source relative to the control section of the endoscope is set so that the switch positions with the desired functions are selectively arranged at optimum positions to further improve the operability and usability of the endoscope apparatus.

Particularly, in this embodiment, the switch ON positions are positions suitable for the two gripping methods including the method in which the light source is gripped with the insertion portion 5 of the endoscope 2 facing downward, and the bending operation lever 14 is operated with the operator's thumb, and the method in which the light source is gripped with the insertion portion 5 of the endoscope 2 arranged horizontally, and the bending operation lever 14 is operated with the operator's forefinger. Therefore, the operator can change the relative position according to conditions, obtaining optimum usability.

Furthermore, the switch OFF position is set at the position in which the battery-powered light source is parallel to the eyepiece portion, and the click mechanism is caused to function at this switch position, thereby facilitating storage and maintenance after use of the battery-powered light source connected to the control section of the endoscope.

Furthermore, in the state in which a battery room containing dry batteries is closed with a cover body, both poles of the dry batteries are elastically held between two contact members of a coil spring provided in the battery room and an electrically conductive panel to establish an electrically conductive state. Therefore, even when an external strong impact is applied to the battery-powered light source to move the dry batteries contained therein by force of inertia, the electrically contact state with the dry batteries can be securely maintained by elastic force.

Therefore, even when an external impact is applied to the light source main body 30 to move the dry batteries 33 contained in the battery room 63 during the illumination lamp 21 is lit, there is no contact defect between the electrodes of the batteries 33 and the battery contact points. It is thus possible to prevent a protecting circuit from mistakenly detecting a voltage drop of the power supply as a short circuit and from turning off the illumination lamp, thereby preventing an operation error of the protecting circuit.

In this embodiment, a malfunction of the protecting circuit is prevented by the two springs serving as elastic arms and including the coil spring 44 and the electrically conductive panel 47. However, by providing an impact absorbing member 68 above the lamp room 36 as shown in FIG. 2, the occurrence of force of inertia in the direction to press the coil spring 44 can be decreased even when an external impact is applied. Therefore, the electrically conductive panel 47 is made unnecessary Also, when the dry batteries are loaded in a wrong direction, electrical connection is avoided by a combination of the electrically conductive plate of the cover body, the electrically conductive panel and the projection of the cover body. It is thus possible to securely prevent a reverse current from flowing in the circuit when the dry batteries are loaded in a wrong direction, thereby preventing a failure due to an error in loading of the dry batteries.

Furthermore, a screw main body of a connecting ring for connecting and fixing the battery-powered light source to the endoscope comprises a metal member and has a portion projecting at an end thereof so as to be elastically abutted against the control section of the endoscope in screw engagement, and the outer periphery is covered with a screw cover made of a rubber material. Therefore, during operation, loosening of the connecting ring can be securely prevented.

Thus, it is possible to prevent the convergence efficiency of light from the illumination lamp 21 to the light guide incidence portion from deteriorating due to an uncertain connection state, thereby preventing darkening of observation light. Also, the temperature of the outer surface of the connecting ring 24 is prevented from being increased by the heat of the illumination lamp 21.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A battery-powered light source in which a relative position to a control section of an endoscope is changed to switch an illumination lamp to an ON state or OEF state, the battery-powered light source comprising:

a light source main body containing a battery for supplying electric power for turning on the illumination lamp;

a plurality of switch positions provided in a range in which the relative position between the light source main body and the control section of the endoscope is changed; and a click mechanical portion provided at at least one of the switch positions, for maintaining the relative position between the light source main body and the control section of the endoscope in a predetermined state and switching the illumination lamp to a predetermined state while maintaining the state of the relative position wherein at a switch position in which the direction of the lonaitudinal axis of the light source main body held by the click mechanical portion is substantially parallel to the direction of the lonaitudinal axis of the control section of the endoscope, the illumination lamp is in a first predetermined state and, at opposite symmetric switch positions in which the direction of the lonaitudinal axis of the light source main body is substantially perpendicular to the direction of the longitudinal axis of the control section of the endoscope, the illumination lamp is in a second predetermined state.

2. The battery-powered source according to claim 1, wherein the light source main body is rotated with respect to the control section of the endoscope to change the relative position.

3. The battery-powered light source according to claim 1, wherein when switched to said first predetermined state the illumination lamp is turned off.

4. The battery-powered light source according to claim 3 wherein when switched to said second predetermined state the illumination lamp is turned on.

5. An endoscope apparatus in which a relative position between a control section of an endoscope and a battery-powered light source is changed to switch an illumination lamp to an ON state or OFF state, the endoscope apparatus comprising:

an endoscope comprising a light guide for guiding illumination light illuminating an inspection site, a control section, and an illumination light incidence end surface arranged in the control section; and a battery-powered light source connected to the vicinity of the illumination light incidence end surface of the control section of the endoscope;

wherein the battery-powered light source comprises:

an illumination lamp disposed opposite the illumination light incidence end surface to emit the illumination light;

a battery for supplying electric power for turning on the illumination lamp;

a light source main body for containing the battery; a switch position to which the relative position of the light source main body to the control section of the endoscope is moved in a predetermined range to switch the illumination lamp to the ON state or the OFF state; and a click mechanical portion provided at the switch position to which the relative position of the light source main body to the control section of the endoscope is moved in the predetermined range, for click-fixing the light source main body wherein at a switch position in which the direction of the longitudinal axis of the light source main body held by the click mechanical portion is click-fixed substantially parallel to the direction of the longitudinal axis of the control section of the endoscope, the illumination lamp is in one of said ON state or OFF state and, at switch positions symmetrical with respect to the longitudinal axis of the control section of the endoscope, the illumination lamp is in the other of said ON state or OFF state.

6. The endoscope apparatus according to claim 5, wherein the battery-powered light source is detachably connected to the control section of the endoscope.

7. The endoscope apparatus according to claim 5, wherein the light source main body is rotated around a straight line perpendicular to the longitudinal axis of the control section of the endoscope as a central axis in a predetermined angular range with respect to the longitudinal axis of the control section; and the switch position is a position to which the longitudinal axis of the light source main body is rotated by a predetermined angle relative to the longitudinal axis of the control section, and when the light source main body is arranged at the switch position, the illumination lamp is turned on or off.

8. The endoscope apparatus according to claim 5, wherein the positional relationship in which the longitudinal axis of the light source main body click-fixed by the click mechanical portion is substantially parallel to the longitudinal axis of the control section, the illumination lamp is turned off.

9. The endoscope apparatus according to claim 5, wherein at said symmetric switch positions with respect to the longitudinal axis of the control sections the illumination lamp is turned on.

10. An endoscope apparatus in which a relative position between a control section of an endoscope and a battery-powered light source is changed to switch an illumination lamp to an ON state or OFF state, the endoscope apparatus comprising:

an endoscope comprising a light guide for guiding illumination light illuminating an inspection site, a control section, and an illumination light incidence end surface arranged in the control section; and a battery-powered light source detachably connected to the vicinity of the illumination light incidence end surface of the control section of the endoscope;

wherein the battery-powered light source comprises:

an illumination lamp disposed opposite the illumination light incidence end surface to emit the illumination light;

a lamp receiving unit containing the illumination lamp;

a battery for supplying electric power for turning on the illumination lamp;

a light source main body provided for containing the battery so as to be rotatable around the longitudinal axis of the lamp receiving unit with respect to the lamp receiving unit;

at least three switch positions provided in a range in which the light source main body is rotated, for switching the illumination lamp to the ON state or the OFF state; and a click mechanical portion provided at the switch position at a predetermined rotation position in the rotational range, for click-fixing the light source main body to the lamp receiving unit wherein a switch position in which the direction of the longitudinal axis of the light source main body held by the click mechanical portion is click-fixed substantially parallel to the direction of the longitudinal axis of the control section of the endoscope, the illumination lamp is in one of said ON state or OFF state and, at a switch position at a respective end of the rotational range symmetric with respect to the direction of the longitudinal axis of the control section of the endoscope, the illumination lamp is in the other of said ON state or OFF state.

11. The endoscope apparatus according to claim 10, wherein at least two switch positions are provided at the ends of the rotational range, and are symmetric with respect to the longitudinal axis of the light source main body arranged at the switch position where the click mechanical portion is provided.

12. The endoscope apparatus according to claim 11, wherein at each of the two switch positions provided at the ends of the rotational range, the illumination lamp is turned on.

* * * * *